United States Patent [19]

Tanaka et al.

[11] Patent Number: 4,672,127
[45] Date of Patent: Jun. 9, 1987

[54] PROCESS FOR PRODUCTION OF HYDANTOIN DERIVATIVES

[75] Inventors: Jun Tanaka; Kazuo Nakayasu, both of Kanagawa, Japan

[73] Assignee: Showa Denko Kabushiki Kaisha, Tokyo, Japan

[21] Appl. No.: 760,425

[22] Filed: Jul. 30, 1985

[51] Int. Cl.$^4$ .................. C07D 233/74; C07D 233/78; C07D 233/76
[52] U.S. Cl. .................................................... 548/308
[58] Field of Search ........................................ 548/308

[56] References Cited

U.S. PATENT DOCUMENTS 4,175,198 11/1979 Gaudette ............................. 548/308
4,345,072 8/1982 Kleeman et al. ................ 548/309 X

FOREIGN PATENT DOCUMENTS 37480 10/1981 European Pat. Off. ............ 548/308

Primary Examiner—Richard A. Schwartz
Attorney, Agent, or Firm—Sughrue, Mion, Zinn, Macpeak, and Seas

[57] ABSTRACT

Hydantoin derivatives are industrially advantageously produced at a high yield by reacting hydantoin with carbonyl compounds in the presence of (i) amino acids or the salts thereof and (ii) inorganic alkali compounds for a relatively short reaction time in an aqueous medium.

8 Claims, No Drawings

PROCESS FOR PRODUCTION OF HYDANTOIN DERIVATIVES

BACKGROUND OF THE INVENTION

1. Field of the Invention

The present invention relates to a novel production process of hydantoin derivatives, which are useful as intermediates for the production of pharmaceutical chemicals such as α-keto carboxylic acids and amino acids including phenylalanine.

2. Description of the Related Art

Typically, 5-substituted hydantoins are produced by a so-called Wheeler-Hoffman process (see J. Am. Chem, Soc., 45, 369 (1911)). According to this process, carbonyl compounds, especially aldehydes and hydantoins are condensated in the presence of acetic acid and anhydrous sodium acetate. Furthermore, this reaction can be carried out in the presence of anhydrous piperazine (see Org. Syn., Coll. Vol. 5, 627).

These processes are, however, disadvantageous from the industrial point of view in that expensive organic solvents must be used in the reaction and the yield of the desired hydantoin derivatives is as low as approximately 70%.

SUMMARY OF THE INVENTION

Accordingly, the objects of the present invention are to eliminate the above-mentioned disadvantages of the prior art and to provide a process for industrially advantageously producing hydantoin derivatives (i.e., 5-substituted hydantoins) having good crystallizability, at a high yield and in a relatively short reaction time in an aqueous medium.

Other objects and advantages of the present invention will be apparent from the description set forth hereinbelow.

In accordance with the present invention, there is provided a process for producing a hydantoin derivative comprising reacting hydantoin with a carbonyl compound in the presence of (i) an amino acid or the salt thereof and (ii) an inorganic alkali compound in an aqueous medium.

DESCRIPTION OF THE PREFERRED EMBODIMENTS

According to the present invention, the desired hydantoin derivatives can be produced at a high yield by reacting hydantoin (i.e., 2,4-imidazolidinedione) with carbonyl compounds in the presence of (i) amino acids or the salts thereof and (ii) inorganic alkali compounds in an aqueous medium in a relatively short reaction time without forming a substantial amount of unpreferable by-products.

The present reaction can be represented as follows:

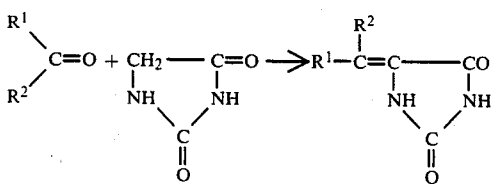

wherein $R^1$ and $R^2$ are independently an alkyl group, preferably having 1 to 4 carbon atoms, or $R^1$ is hydrogen and $R^2$ is an alkyl group preferably having 1 to 5 carbon atoms or a phenyl group, which may be substituted with one or more substituents such as a halogen atom, a hydroxyl group, a lower alkyl group, a lower alkoxy group, a lower alkylmercapto group, a lower alkanoyl group or a lower alkanoylamino group (the two substituents may be the same or different, or may be bonded together to form a cyclic group).

Examples of the carbonyl compounds usable as a starting compound in the present process are benzaldehyde; aryl aldehydes such as p-hydroxy benzaldehyde, 3,4-dihydroxy benzaldehyde, p-methoxy benzaldehyde, p-methyl benzaldehyde, o-hydroxy benzaldehyde, 3,4-methylenedihydroxy benzaldehyde, p-ethyl benzaldehyde, p-isopropyl benzaldehyde, p-acetoxy benzaldehyde, p-acetoamino benzaldehyde, p-methylthio benzaldehyde, p-chloro benzaldehyde, and p-fluoro benzaldehyde; aldehydes having the general formula:

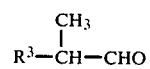

wherein $R^3$ is an alkyl group having 1 to 3 carbon atoms, such as, for example, isobutyl aldehyde, 2-methylbutyl aldehyde, 2-methylamyl aldehyde, and 2,3-dimethylbutyl aldehyde; and ketones having the general formula:

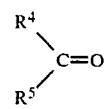

wherein $R^4$ and $R^5$ are independently an alkyl group having 1 to 4 carbon atoms, such as, for example, acetone, methyl ethyl ketone, diethyl ketone, methyl propyl ketone, methyl isopropyl ketone, methyl butyl ketone, and methyl isobutyl ketone. Although there are no critical limitations between the reaction amounts of hydantoin and the carbonyl compound, the carbonyl compound is preferably used in an amount of 1.0 to 5.0 mol, more preferably 1.0 to 2.0 mol, based on 1 mol of hydantoin.

Examples of the amino acids usable in the present invention are glutamic acid, aspartic acid, lysine, arginine, ornithine, glycine, α-alanine, leucine, isoleucine, valine, β-alanine, phenylalanine, tyrosine, dopa, phenylglycine, serine, threonine, methionine, taurine, S-carboxymethylcysteine, γ-aminobutyric acid, tranexmic acid 3-aminocyclohexanecarboxylic acid, and their salts (e.g., alkali metal salts such as sodium salts, and potassium salts, alkaline earth metal salts such as calcium salts, and mineral acid salts such as hydrochloric acid salts and sulfuric acid salts). These compounds can be used alone or in any mixture thereof.

Although there are no critical limitations to the amounts of the amino acids or the salts thereof, the amino acids or the salts thereof are preferably used in an amount of 0.1 to 2 mol, more preferably 0.3 to 1 mol, based on 1 mol of the hydantoin. The use of too small an amount of the amino acids or the salts thereof does not result in the desired yield, whereas the use of too large an amount of the amino acids or the salts thereof does not further improve the yield of the desired compound and, therefore, is not economical.

Examples of the inorganic alkali compounds usable in the present process are alkali metal hydroxides such as sodium hydroxide and potassium hydroxide, alkali metal carbonates such as sodium carbonate and potassium carbonate, alkali metal bicarbonates such as sodium bicarbonate and potassium bicarbonate, alkali metal sulfites such as sodium sulfite, and alkaline earth metal hydroxides such as magnesium hydroxide and calcium hydroxide. The preferable alkali compounds are sodium hydroxide and potassium hydroxide from the practical points of view. Of course, it should be noted that there are no critical limitations to the kind of the alkali compounds.

These alkali compounds are generally used in an amount such that the pH of the reaction mixture is made to 8 to 12, preferably 9 to 10. This is because, when the amino acid is used in an acidic or neutral condition, the desired improvement cannot be obtained. For instance, when benzaldehyde is reacted with hydantoin in the presence of glycine, the alkali compound is generally used in an amount of 0.05 to 2 mol, preferably 0.1 to 1 mol, based on 1 mol of the glycine. If it is necessary to use an acid for the pH adjustment, a mineral acid such as hydrochloric acid or sulfuric acid or an organic acid such as formic acid or acetic acid should be used.

According to the present process, the above-mentioned reaction can be carried out in an aqueous medium such as water or an aqueous solution containing a hydrophilic solvent. Examples of such hydrophilic solvents are alcohols such as methanol, ethanol, propanol, ethylene glycol, trimethylene glycol and triethylene glycol, and dioxane.

Furthermore, although there are no critical limitations to the reaction temperature, the reaction pressure, and the reaction time, the present reaction is preferably carried out at a temperature of approximately 40° C. to 100° C., more preferably 60° C. to 80° C., under a pressure of 1 to 10 atm, more preferably 1 to 2 atm for 1 to 10 hours, more preferably 2 to 5 hours.

According to the present process, the resultant 5-substituted hydantoin derivatives such as 5-benzylidene hydantoin, 5-arylidene hydantoin, and 5-alkylidene hydantoin precipitate as crystals in the reaction medium with the progress of the reaction, since these hydantoin derivatives are only slightly soluble in water. Therefore, the resultant products can be easily separated and recovered from the reaction mixture by, for example, centrifugal separation.

EXAMPLE

The present invention will now be further illustrated by, but is by no means limited to, the following Examples.

EXAMPLES 1

A 500 ml three-necked flask provided with a thermometer, a reflux condenser, and an agitator was set in a constant temperature bath.

A 37.5 g amount of glycine and 26.5 g of sodium carbonate were dissolved in 200 ml of water in the flask. Then, 53.0 g of benzaldehyde and 50.0 g of hydantoin were added to the resultant solution. The mixture was allowed to react at a temperature of 100° C. for 1 hour while stirring. During the reaction, the pH of the reaction mixture was 9.7 to 9.4. After cooling, the precipitated 5-benzylidene hydantoin was separated and recovered from the reaction mixture. Thus, 83.0 g of 5-benzylidene hydantoin was obtained. The yield was 88% based on the hydantoin.

EXAMPLE 2

A 200 ml amount of water, 18.8 g of glycine, and 7.0 g of potassium hydroxide were added to the apparatus used in Example 1. After the mixture was dissolved, 53.0 g of benzaldehyde and 50.0 g of hydantoin were added to the solution. The mixture was then allowed to react at a temperature of 80° C. for 2 hours while stirring. During the reaction, the pH of the reaction mixture was 9.6 to 9.3.

After cooling the reaction mixture, the precipitated 5-benzylidene hydantoin was separated and recovered from the reaction mixture. Thus, 86.1 g of 5-benzylidene hydantoin was obtained. The yield was 92% based on the hydantoin.

EXAMPLE 3

A 200 ml amount of water, 40 ml of ethanol, 18.8 g of glycine, and 3.0 g of sodium hydroxide were added to the apparatus used in Example 1. Furthermore, 53.0 g of benzaldehyde and 50.0 g of hydantoin were added to the mixture. The mixture was then allowed to react at a temperature of 70° C. for 4 hours while stirring. During the reaction, the pH of the reaction mixture was 9.3 to 9.1.

After cooling, the precipitated 5-benzylidene hydantoin was separated and recovered from the reaction mixture. Thus, 88.3 g of 5-benzylidene hydantoin was obtained. The yield was 94% based on the hydantoin.

COMPARATIVE EXAMPLE 1

A 200 ml amount of water and 37.5 g of glycine were added to the apparatus used in Example 1. After the glycine was dissolved in water, 53.0 g of benzaldehyde and 50.0 g of hydantoin were added to the solution. The mixture was then allowed to react at a temperature of 100° C. for 12 hours while stirring. During the reaction, the pH of the reaction mixture was 6.5 to 5.5.

After cooling, the precipitated 5-benzylidene hydantoin was separated and recovered from the reaction mixture. The yield was 53.7 g (57% based on the hydantoin).

COMPARATIVE EXAMPLE 2

A 200 ml amount of water and 10.0 g of sodium hydroxide were added to the apparatus used in Example 1. After the mixture was dissolved, 53.0 g of benzaldehyde and 50.0 g of hydantoin were added to the solution. The mixture was then allowed to react at a temperature of 80° C. for 12 hours while stirring. During the reaction, the pH of the reaction mixture was 13.0 to 12.5.

After cooling, the precipitated 5-benzylidene hydantoin was separated and recovered from the reaction mixture. The yield was 36.6 g (39% based on the hydantoin).

EXAMPLE 4

A 500 ml three-necked separable flask provided with a thermometer, a reflux condenser, and an agitator was set in a constant temperature bath.

A 200 ml amount of water, 50.0 g (0.50 mol) of hydantoin, 18.8 g (0.25 mol) of glycine, 5.0 g (0.125 mol) of solid sodium hydroxide, and 61.1 g (0.50 mol) of p-hydroxybenzaldehyde were charged into the flask. The mixture was heated, while stirring, at a temperature of 80° C. for 2 hours. During the reaction, the pH of the reaction mixture was 9.8 to 9.6.

After cooling to room temperature, 93.0 g of 5-p-hydroxybenzylidene hydantoin was obtained by centrifugal separation. The yield based on the hydantoin was 91.2%.

EXAMPLE 5

5-(3,4-Dihydroxybenzylidene)-hydantoin was prepared in the same manner as in Example 4, except that 45.7 g (0.25 mol) of L-lysine.hydrochloride and 69.1 g (0.50 mol) of 3,4-dihydroxybenzaldehyde were used in lieu of glycine and p-hydroxybenzaldehyde, respectively. During the reaction, the pH of the reaction mixture was 9.4 to 9.2.

Thus, 102.5 g of 5-(3,4-dihydroxybenzylidene)hydantoin was obtained. The yield was 93.2% based on the hydantoin.

EXAMPLE 6

5-(p-Methoxybenzylidene)-hydantoin was prepared in the same manner as in Example 4, except that 46.8 g (0.25 mol) of sodium L-glutamate.monohydrate and 68.1 g (0.50 mol) of p-methoxybenzaldehyde were used in lieu of glycine and p-hydroxybenzaldehyde, respectively. During the reaction, the pH of the reaction mixture was 9.9 to 9.7.

Thus, 104.5 g of 5-(p-methoxybenzylidene)-hydantoin was obtained. The yield was 95.9% based on the hydantoin.

EXAMPLE 7

5-(p-Methylbenzylidene)-hydantoin was prepared in the same manner as in Example 4, except that 31.3 g (0.25 mol) of taurine and 60.0 g (0.50 mol) of p-tolualdehyde were used in lieu of glycine and p-hydroxybenzaldehyde, respectively. During the reaction, the pH of the reaction mixture was 9.8 to 9.6.

Thus, 94.5 g of 5-(p-methylbenzylidene)-hydantoin was obtained. The yield was 93.6% based on the hydantoin.

EXAMPLE 8

5-(o-Hydroxybenzylidene)-hydantoin was prepared in the same manner as in Example 4, except that 22.2 g (0.25 mol) of β-alanine and 61.1 g (0.50 mol) of o-hydroxybenzaldehyde were used in lieu of glycine and p-hydroxybenzaldehyde, respectively, and that the reaction time was 6 hours. During the reaction, the pH of the reaction mixture was 9.6 to 9.2.

Thus, 89.3 g of 5-(o-hydroxybenzylidene)-hydantoin was obtained. The yield was 87.5% based on the hydantoin.

EXAMPLE 9

5-(3,4-Methylenedioxybenzylidene)-hydantoin was prepared in the same manner as in Example 4, except that 75.0 g (0.50 mol) of 3,4- methylenedioxybenzaldehyde was used in lieu of p-hydroxybenzaldehyde. During the reaction, the pH of the reaction mixture was 9.8 to 9.6.

Thus, 5-(3,4-methylenedioxybenzylidene)-hydantoin was obtained. The yield was 94.1% based on the hydantoin.

EXAMPLE 10

A 500 ml three-necked separable flask provided with a thermometer, a reflux condenser, and an agitator was set in a constant temperature bath.

A 200 ml amount of water, 50.5 g (0.50 mol) of hydantoin, 22.3 g (0.25 mol) of alanine, 5.0 g (0.125 mol) of solid sodium hydroxide, and 53.0 g (0.50 mol) of benzaldehyde were charged into the flask. The mixture was heated and was allowed to react at a temperature of 80° C. for 2 hours while stirring. During this period, the pH of the reaction mixture was 9.8 to 9.6.

After cooling the reaction mixture, 87.0 g of 5-benzylidene hydantoin was obtained by the centrifugal separation of the reaction mixture. The yield was 92.6% based on the hydantoin.

EXAMPLE 11

5-Benzylidene hydantoin was prepared in the same manner as in Example 10, except that 46.8 g (0.25 mol) of sodium L-glutamate.monohydrate was used in lieu of alanine. During the reaction, the pH of the reaction mixture was 9.8 to 9.5.

Thus, 82.5 g of 5-benzylidene hydantoin was obtained. The yield was 87.8% based on the hydantoin.

EXAMPLE 12

5-Benzylidene hydantoin was prepared in the same manner as in Example 10, except that 45.7 g (0.25 mol) of L-lysine.hydrochloride was used in lieu of the alanine and that the pH of the reaction mixture was controlled with potassium hydroxide. The pH of the reaction mixture was 9.6 to 9.3.

Thus, 86.6 g of 5-benzylidene hydantoin was obtained. The yield was 92.1% based on the hydantoin.

EXAMPLE 13

5-Benzylidene hydantoin was prepared in the same manner as in Example 10, except that 13.3 g (0.15 mol) of β-alanine was used in lieu of alanine and that the pH was adjusted with potassium hydroxide. During the reaction, the pH of the reaction mixture was 9.9 to 9.7.

Thus, 79.5 g of 5-benzylidene hydantoin was obtained. The yield was 84.6% based on the hydantoin.

EXAMPLE 14

5-Benzylidene hydantoin was prepared in the same manner as in Example 10, except that 13.3 g (0.15 mol) of L-phenylalanine was used in lieu of alanine and that the reaction time was 10 hours. During the reaction, the pH of the reaction mixture was 9.7 to 9.4.

Thus, 77.0 g of 5-benzylidene hydantoin was obtained. The yield was 81.9% based on the hydantoin.

EXAMPLE 15

5-Benzylidene hydantoin was prepared in the same manner as in Example 10, except that 42.1 g (0.40 mol) of L-serine was used in lieu of alanine. During the reaction, the pH of the reaction mixture was 9.1 to 8.9.

Thus, 75.4 g of 5-benzylidene hydantoin was obtained. The yield was 80.2% based on the hydantoin.

EXAMPLE 16

5-Benzilidene hydantoin was prepared in the same manner as in Example 10, except that 31.3 g (0.25 mol) of taurine was used in lieu of alanine. During the reaction, the pH of the reaction mixture was 9.5 to 9.3.

Thus, 82.7 g of 5-benzylidene hydantoin was obtained. The yield was 88.0% based on the hydantoin.

COMPARATIVE EXAMPLE 3

5-Benzylidene hydantoin was prepared in the same manner as in Example 10, except that the pH of the reaction mixture was kept to 12.5 to 12.0 with 32.0 g (0.80 mol) of sodium hydroxide.

The yield of 5-benzylidene hydantoin was 52.6 g (54.0% based on the hydantoin). After the reaction, no hydantoin was found in the reaction mixture.

COMPARATIVE EXAMPLE 4

5-Benzylidene hydantoin was prepared in the same manner as in Example 10, except that the pH of the reaction mixture was adjusted to 8.0 to 7.5 with 0.7 g (0.018 mol) of sodium hydroxide.

The yield of 5-benzylidene hydantoin was 69.7 g (74.1% based on the hydantoin).

COMPARATIVE EXAMPLE 5

5-Benzylidene hydantoin was prepared in the same manner as in Example 10, except that 8.9 g (0.10 mol) of alanine and 1.0 g (0.05 mol) of sodium hydroxide were used and that the reaction was carried out for 9 hours. The pH of the reaction mixture during the reaction was 8.1 to 7.5.

The yield of 5-benzylidene hydantoin was 72.1 g (76.7% based on the hydantoin).

EXAMPLE 17

A 500 ml separable flask provided with a thermometer, a reflux condenser, and an agitator was set in a constant temperature bath.

A 200 ml amount of water, 50.0 g (0.50 mol) of hydantoin, 58.0 g (1.00 mol) of acetone, 37.5 g (0.50 mol) of glycine, and 10.0 g (0.25 mol) of sodium hydroxide were charged into the flask. The mixture was heated at a temperature of 60° C. to 65° C. for 6 hours while stirring. During the reaction, the pH of the reaction mixture was 9.8 to 9.6.

After cooling, the resultant crystal was recovered by centrifugal separation. Thus, 64.5 g of 5-isopropylidene hydantoin was obtained. The yield was 92.1% based on the hydantoin.

COMPARATIVE EXAMPLE 6

5-Isopropylidene hydantoin was prepared in the same manner as in Example 17, except that the pH of the reaction mixture was adjusted to 12.8 to 12.0 with 33.0 g of sodium hydroxide during the reaction.

After cooling, 17.0 g of 5-isopropylidene hydantoin was obtained. The yield was 24.3% based on the hydantoin.

COMPARATIVE EXAMPLE 7

5-Isopropylidene hydantoin was prepared in the same manner as in Example 17, except that the pH of the reaction mixture was adjusted to 7.5 to 6.8 during the reaction with 2.1 g of sodium hydroxide.

After cooling, 7.5 g of 5-isopropylidene hydantoin was obtained by centrifugal separation. The yield was 10.7%.

EXAMPLE 18

A 500 ml separable flask provided with a thermometer, a reflux condenser, and an agitator were set in a constant temperature bath.

A 200 ml amount of water, 50.0 g (0.50 mol) of hydantoin, 72.1 g (1.00 mol) of isobutylaldehyde, 28.1 g (0.38 mol) of glycine, and 7.5 g (0.19 mol) of sodium hydroxide were charged into the flask. The mixture was heated and was allowed to react at a temperature of 70° C. to 75° C. for 7 hours, while stirring. The pH of the reaction mixture was 9.5 to 9.3 during the reaction.

After cooling the reaction mixture to room temperature, the resultant crystal was recovered by centrifugal separation. Thus, 65.1 g of 5-(2-methylpropylidene)-hydantoin was obtained. The yield was 84.5% based on the hydantoin.

EXAMPLE 19

5-(2-Methylpropylidene)-hydantoin was prepared in the same manner as in Example 18, except that 26.8 g (0.30 mol) of alanine, 8.6 g (0.15 mol) of calcium hydroxide, and 64.6 g (0.75 mol) of 2-methylbutyl aldehyde were used in lieu of glycine, sodium hydroxide, and isobutyl aldehyde, respectively, and that the reaction was carried out at a temperature of 80° C. for 4 hours. The pH of the reaction mixture during the reaction was 9.4 to 9.2.

After cooling the reaction mixture to room temperature, the resultant crystal was recovered by centrifugal separation. Thus, 74.5 g of 5-(2-methylbutylidene)-hydantoin was obtained. The yield was 88.6% based on hydantoin.

COMPARATIVE EXAMPLE 8

5-(2-Methylpropylidene)-hydantoin was prepared in the same manner as in Example 18, except that the pH of the reaction mixture was 12.9 to 12.2 during the reaction with 46.1 g of sodium hydroxide.

After cooling, 24.0 g of the resultant 5-(2-methylpropylidene)-hydantoin was recovered by centrifugal separation. The yield was 31.2% based on the hydantoin.

COMPARATIVE EXAMPLE 9

5-(2-Methylpropylidene)-hydantoin was prepared in the same manner as in Example 18, except that the pH of the reaction mixture was adjusted to 7.6 to 7.0, during the reaction, with 2.7 g of sodium hydroxide.

After cooling, 8.9 g of 5-(2-methylpropylidene)-hydantoin was recovered by centrifugal separation. The yield was 11.5% based on the hydantoin.

We claim:

1. A process for producing a 5-aralkylidene or 5-alkylidene hydantoin derivative comprising
   reacting hydantoin with a carbonyl compound in the presence of
   (i) an amino acid or the salt thereof and
   (ii) an inorganic alkali compound
   in an aqueous medium, the amount of the inorganic alkali compound (ii) being such that the pH of the reaction mixture is kept to 8 to 12 during the reaction.

2. A process as claimed in claim 1, wherein the carbonyl compound is an aryl aldehyde.

3. A process as claimed in claim 2, wherein the carbonyl compound is benzaldehyde.

4. A process as claimed in claim 1, wherein the carbonyl compound is an aldehyde having the following formula:

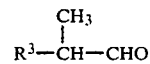

wherein $R^3$ is an alkyl group having 1 to 3 carbon atoms.

5. A process as claimed in claim 1, wherein the carbonyl compound is a ketone having the formula:

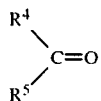

wherein $R^4$ and $R^5$ are independently an alkyl group having 1 to 4 carbon atoms.

6. A process as claimed in claim 1, wherein the carbonyl compound is present in an amount of 1.0 to 5.0 mol, based on 1 mol of the hydantoin.

7. A process as claimed in claim 1, wherein the amino acid is glycine, lysine, glutamic acid, taurine, alanine, phenylalanine, serine, or a salt thereof.

8. A process as claimed in claim 1, wherein the amino acid is present in an amount of 0.1 to 2 mol based on 1 mol of the hydantoin.

* * * * *